United States Patent
Saito et al.

(10) Patent No.: US 11,619,689 B2
(45) Date of Patent: Apr. 4, 2023

(54) OPTICALLY PUMPED MAGNETOMETER HAVING REDUCED FOOTPRINT

(71) Applicants: HAMAMATSU PHOTONICS K.K., Hamamatsu (JP); Kyoto University, Kyoto (JP)

(72) Inventors: Akinori Saito, Hamamatsu (JP); Takahiro Moriya, Hamamatsu (JP); Takenori Oida, Hamamatsu (JP); Motohiro Suyama, Hamamatsu (JP); Tetsuo Kobayashi, Kyoto (JP)

(73) Assignees: HAMAMATSU PHOTONICS K.K., Hamamatsu (JP); Kyoto University, Kyoto (JP)

( * ) Notice: Subject to any disclaimer, the term of this patent is extended or adjusted under 35 U.S.C. 154(b) by 53 days.

(21) Appl. No.: 17/346,322

(22) Filed: Jun. 14, 2021

(65) Prior Publication Data
US 2021/0389396 A1   Dec. 16, 2021

(30) Foreign Application Priority Data
Jun. 16, 2020 (JP) .............................. JP2020-103957

(51) Int. Cl.
*G01R 33/26* (2006.01)

(52) U.S. Cl.
CPC ................... *G01R 33/26* (2013.01)

(58) Field of Classification Search
CPC .. G01R 33/26; G01R 33/0094; G01R 33/032; A61B 5/245
See application file for complete search history.

(56) References Cited

U.S. PATENT DOCUMENTS

| | | | |
|---|---|---|---|
| 2014/0121491 A1* | 5/2014 | Zhang | A61B 5/6814 600/409 |
| 2016/0154072 A1* | 6/2016 | Nagasaka | G01R 33/0322 324/304 |
| 2018/0210039 A1* | 7/2018 | Shalev | G01V 3/165 |
| 2020/0064421 A1 | 2/2020 | Kobayashi et al. | |
| 2020/0110141 A1 | 4/2020 | Kato et al. | |

FOREIGN PATENT DOCUMENTS

| | | |
|---|---|---|
| JP | 5823195 B2 | 11/2015 |
| JP | 2020-030161 A | 2/2020 |
| JP | 2020-030162 A | 2/2020 |
| JP | 2020-060378 A | 4/2020 |

* cited by examiner

*Primary Examiner* — Jay Patidar
(74) *Attorney, Agent, or Firm* — Faegre Drinker Biddle & Reath LLP

(57) ABSTRACT

An optically pumped magnetometer 1 includes: a cell 2; a pump laser 7 that emits pump light; one or more pump light mirrors that cause the pump light guided in a first direction; a probe laser 8 that emits probe light; a splitting unit 12 that splits the probe light into multiple light components; one or more probe light mirrors that cause each of the probe light components guided in a second direction, which is a direction perpendicular to the first direction; a detection unit that detects each of the probe light components perpendicular to the pump light inside the cell 2; and a derivation unit that derives a magnetic field corresponding to a region where each of the probe light components and the pump light are perpendicular to each other based on a detection result of the detection unit.

14 Claims, 8 Drawing Sheets

OPTICALLY PUMPED MAGNETOMETER HAVING REDUCED FOOTPRINT

TECHNICAL FIELD

Aspects of the present invention relate to an optically pumped magnetometer.

BACKGROUND

In the related art, as a magnetoencephalograph, a superconducting quantum interference device (SQUID) has been used to measure a small magnetic field of the brain. In recent years, a magnetoencephalograph using an optically pumped magnetometer instead of the SQUID has been studied. The optically pumped magnetometer measures a small magnetic field of the brain by using the spin polarization of alkali metal atoms excited by optical pumping. For example, Japanese Patent No. 5823195 discloses a magnetoencephalograph using an optically pumped magnetometer.

SUMMARY

In a magnetoencephalograph using an optically pumped magnetometer, for example, 100 or more optically pumped magnetometers are arranged along the scalp. However, since the footprint of the known optically pumped magnetometer has a size of about 20×20 $mm^{2'}$, it is not possible to reduce the interval (pitch) between measurement locations when multiple optically pumped magnetometers are arranged.

Therefore, it is an object of aspects of the present invention to provide an optically pumped magnetometer capable of reducing the interval between measurement locations.

An optically pumped magnetometer according to one aspect of the present invention includes: a cell that is arranged along a measurement target and is filled with vapor of an alkali metal; a pump laser that emits pump light for exciting an atom of the alkali metal; one or more pump light mirrors that reflect the pump light emitted from the pump laser and cause the pump light guided in a first direction along the measurement target to be incident on the cell; a probe laser that emits probe light for detecting a change in a polarization angle caused by a magnetic field in an excited state of the alkali metal atom; a splitting unit that splits the probe light into multiple light components; one or more probe light mirrors that reflect probe light components, which are obtained as a result of the splitting by the splitting unit, and cause each of the probe light components guided in a second direction along the measurement target, which is a direction perpendicular to the first direction, to be incident on the cell; a detection unit that detects each of the probe light components perpendicular to the pump light inside the cell; and a derivation unit that derives a change in the polarization angle corresponding to each of the probe light components based on a detection result of the detection unit and derives a magnetic field, which is relevant to a measurement location corresponding to a region where each of the probe light components and the pump light are perpendicular to each other, from the change in the polarization angle corresponding to each of the probe light components.

In the optically pumped magnetometer according to one aspect of the present invention, the pump light guided in the first direction along the measurement target is incident on the cell filled with alkali metal vapor, and each of the multiple probe light components obtained as a result of the splitting by the splitting unit and guided in the second direction along the measurement target, which is a direction perpendicular to the first direction, is incident on the cell filled with alkali metal vapor. Then, by deriving the change in the polarization angle caused by the spin polarization corresponding to each probe light component passing through the cell, the magnetic field corresponding to the region where the pump light and each probe light component are perpendicular to each other inside the cell is derived. As described above, in the optically pumped magnetometer according to one aspect of the present invention, since the probe light is split into multiple light components, it is not necessary to prepare the probe laser for each region where the pump light and each probe light component are perpendicular to each other. Therefore, the configuration of the probe laser is simplified. In addition, in such an optically pumped magnetometer, the probe light is split into multiple light components, and multiple channels are measured inside a single cell. Therefore, compared with a case where the probe light is not split, the interval between the measurement locations can be reduced. As described above, according to one aspect of the present invention, it is possible to provide the optically pumped magnetometer capable of reducing the interval between the measurement locations.

The probe laser may emit probe light whose height is smaller than its width. By emitting the probe light having a large width in this manner, the region where the pump light and the probe light are perpendicular to each other becomes large. Therefore, it is possible to improve the measurement accuracy of the optically pumped magnetometer.

The alkali metal may be potassium and rubidium, the pump laser may excite an atom of the rubidium for spin polarization, and to be transferred to that of the potassium, and the probe laser may emit probe light for detecting a change in a polarization angle caused by a magnetic field in an excited state of the potassium atom. According to such a configuration, when the pump light excites the rubidium atom, the spin polarization of the rubidium atom transfers to the potassium atom to excite the potassium atom. By using such a spin exchange interaction between potassium and rubidium, the potassium atom can be uniformly excited as compared with a case where only the potassium atom is excited. In addition, by using potassium having a high magnetic field sensitivity among alkali metals, it is possible to improve the measurement accuracy of the optically pumped magnetometer.

The pump light and each of the probe light components may be perpendicular to each other in the vicinity of a surface, on which a magnetic field is incident, inside the cell. According to such a configuration, since the pump light and each probe light component are perpendicular to each other at a position where the magnetic field is more strongly received, it is possible to improve the measurement accuracy of the optically pumped magnetometer.

At least one of the pump light mirrors and at least one of the probe light mirrors may be bonded to the cell with an adhesive. According to such a configuration, since the pump light mirror and the probe light mirror are fixed to the cell, there is no space between the cell and each of the mirrors. As a result, the mirrors can be arranged stably and compactly.

The splitting unit may be arranged on a side opposite to the measurement target with the cell interposed therebetween. The probe laser may emit the probe light so that the probe light guided in a direction opposite to the first direction is incident on the splitting unit. The splitting unit may output each of the split probe light components in a direction perpendicular to the first direction and along the measurement target. One of the two probe light mirrors may reflect each of the probe light components, which are obtained as a result of the splitting by the splitting unit, in a direction toward the measurement target, and the other one of the two probe light mirrors may further reflect each of the probe light components reflected by the one probe light mirror in the second direction and cause each of the probe light components to be incident on the cell. According to such a configuration, it is possible to set the optical path of the probe light along the surface of the cell. Since the optical path of the probe light is set along the surface of the cell, the space is saved. Therefore, it is possible to reduce the size of the optically pumped magnetometer.

The optically pumped magnetometer according to one aspect of the present invention may further include: a first member for reference which is filled with the alkali metal vapor and is arranged on a side opposite to the measurement target with the cell interposed therebetween, on which first light for reference guided in the first direction is incident in order to excite the alkali metal atom, and on which multiple second light components for reference guided in the second direction are incident in order to detect a change in the polarization angle caused by a magnetic field in the excited state of the alkali metal atom; and a second member for reference that detects the multiple second light components for reference perpendicular to the first light for reference inside the first member for reference, outside the first member for reference. Each region where each of the probe light components and the pump light are perpendicular to each other in the cell overlaps a region where any of the second light components for reference and the first light for reference are perpendicular to each other in the first member for reference, in a direction perpendicular to the measurement target. When deriving a change in the polarization angle corresponding to each of the probe light components detected by the detection unit, the derivation unit performs noise removal processing in consideration of a detection result of the detection unit with respect to each of the probe light components and a detection result of the second member for reference with respect to the second light for reference whose region overlaps each of the probe light components in the direction perpendicular to the measurement target. The optically pumped magnetometer is configured as a first-order differential axial gradiometer. According to such a configuration, since the influence of the common mode noise is shown in the detection result of the detection unit with respect to each probe light component and the detection result of the second member for reference with respect to the second light for reference, the common mode noise can be removed by acquiring the difference between both the output results. As a result, it is possible to improve the measurement accuracy of the optically pumped magnetometer.

The pump laser may emit the pump light in the same direction as an emission direction of the probe light from the probe laser. According to such a configuration, since a pump light inlet and a probe light inlet are arranged at one place or places close to each other, the configuration of the optically pumped magnetometer can be simplified.

The pump laser may emit the pump light in a direction perpendicular to an emission direction of the probe light from the probe laser. In the region where the pump light and the probe light are perpendicular to each other inside the cell, the emission directions of the pump laser and the probe laser are perpendicular to each other.

Therefore, it is possible to simplify the configuration of the mirrors including the pump light mirror and the probe light mirror.

According to one aspect of the present invention, it is possible to provide an optically pumped magnetometer capable of reducing the interval between the measurement locations.

DETAILED DESCRIPTION

Figures 1A, 1B:
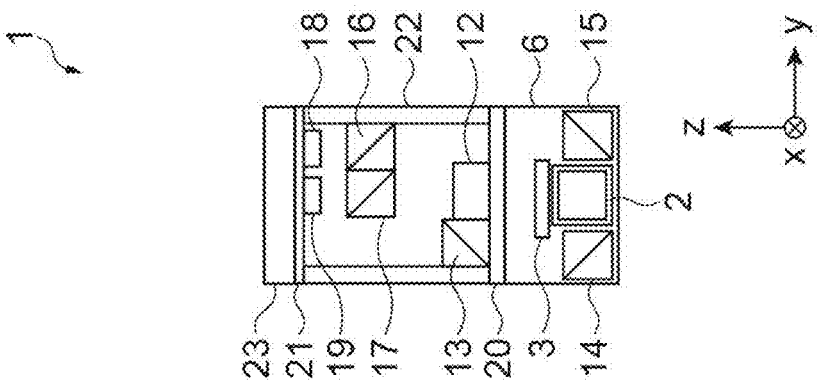
FIGS. 1A and 1B are diagrams showing the configuration of an optically pumped magnetometer.

Hereinafter, an embodiment for carrying out the present invention will be described in detail with reference to the accompanying diagrams. In the description of the diagrams, the same elements are denoted by the same reference numerals, and the repeated description thereof will be omitted.

FIGS. 1A and 1B are diagrams showing the configuration of an optically pumped magnetometer 1. The optically pumped magnetometer 1 is a device that measures a magnetic field using optical pumping. In this specification, the optically pumped magnetometer 1 will be described as being used for the measurement of the brain's magnetic field. However, the application is not limited to this. The x axis and the y axis in FIGS. 1A and 1B are parallel to the scalp (measurement target), and the z axis is perpendicular to the scalp. FIGS. 1A and 1B show the configuration of the optically pumped magnetometer 1 when the optically pumped magnetometer 1 is viewed from different angles. That is, FIG. 1A is a side view of the optically pumped magnetometer 1, and FIG. 1B is a front view of the optically pumped magnetometer 1.

The optically pumped magnetometer 1 includes a cell 2, a heater 3, a thermocouple 5, a case 6, a pump laser 7, a probe laser 8, a fiber connector 9, a mirror 10, a mirror 11, a splitting unit 12, a mirror 13, a mirror 14, a mirror 15, a polarized beam splitter 16, a mirror 17, a first photodiode 18, a second photodiode 19, a peak frame 20, a printed circuit board 21, a peak column 22, and a heat sink 23.

As shown in FIG. 1A, the cell 2 is arranged along the scalp and is filled with alkali metal vapor. The cell 2 can be formed of a material, such as quartz, sapphire, silicon, Kovar glass, and borosilicate glass. The cell 2 allows pump light and probe light, which will be described later, to be transmitted therethrough. Here, the details of the cell 2 will be described with reference to FIG. 2.

Figure 2:
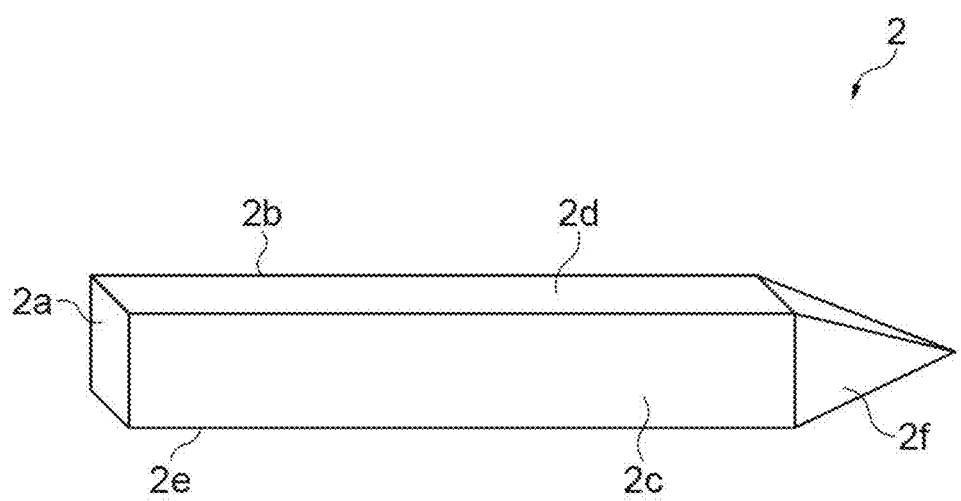
FIG. 2 is a schematic diagram showing the shape of a cell.
Figure 2:
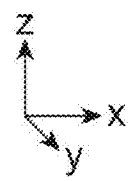

FIG. 2 is a schematic diagram showing the shape of the cell 2. The cell 2 has an approximately rectangular parallelepiped shape and a bottomed tubular shape. The cross section of the cell 2 in a direction perpendicular to the x-axis direction is, for example, a square. A pump light incidence surface 2a, which is one end of the cell 2, is a flat surface on which pump light guided in the positive direction of the x axis is incident. A probe light incidence surface 2b, which is a side surface of the cell 2, is a flat surface on which multiple probe light beams guided in the positive direction of the y axis are incident. A probe light emitting surface 2c, which is a side surface of the cell 2, is a flat surface from which multiple probe light beams guided in the positive direction of the y axis are emitted after passing through the inside of the cell 2. The upper surface 2d of the cell 2 is a flat surface to which the heater 3 or the like, which will be described later, is attached. A magnetic field incidence surface 2e, which is the lower surface of the cell 2, is a flat surface on which a magnetic field in the positive direction of the z axis generated from the brain is incident. The other end of the cell 2 may be a flat surface, or a sealing portion 2f whose diameter decreases gradually in the positive direction of the x axis may be formed at the other end of the cell 2.

The cell 2 contains the vapor of the alkali metal and the filled gas. The alkali metal contained in the cell 2 may be, for example, at least one of lithium (Li), sodium (Na), potassium (K), rubidium (Rb), and cesium (Cs). The alkali metal contained in the cell 2 may be potassium and rubidium, or may be potassium alone. Potassium has a relatively low spin-destruction collision relaxation rate among the alkali metals used in the optically pumped magnetometer. The spin-destruction collision relaxation rate of potassium is lower than those of, for example, cesium, rubidium, and the like. Therefore, when a single alkali metal is adopted, an optically pumped magnetometer using only potassium is more sensitive than an optically pumped magnetometer using only cesium or rubidium.

The filled gas suppresses the relaxation of spin polarization of the alkali metal vapor. In addition, the filled gas protects the alkali metal vapor and suppresses noise emission. The filled gas may be, for example, an inert gas such as helium (He), neon (Ne), argon (Ar), krypton (Kr), xenon (Xe), and nitrogen ($N_2$). The filled gas may be, for example, helium and nitrogen.

Returning to FIG. 1A, the heater 3 and the thermocouple 5 are attached to the cell 2. The heater 3 generates heat according to the current supplied from a heater power supply (not shown). The thermocouple 5 measures the internal temperature of the cell 2. The heater 3 controls the vapor density of the alkali metal by controlling the internal temperature of the cell 2. For example, when potassium and rubidium are contained as alkali metals in the cell 2, the heater 3 heats the cell 2 so that the internal temperature of the cell 2 becomes 180° C. The heater 3 is attached to, for example, the upper surface 2d of the cell 2. The thermocouple 5 is attached to, for example, the probe light incidence surface 2b or the probe light emitting surface 2c of the cell 2 at a position that does not block the optical path of the probe light.

The pump laser 7 emits pump light for exciting the atoms of an alkali metal. The pump laser 7 may shape the pump light in any size. The alkali metal atoms contained in the cell 2 are excited by the pump light, and the spin directions are aligned (spin polarization). The wavelength of the pump light is set according to the type of atoms forming the alkali metal vapor (more specifically, the wavelength of the absorption line).

The pump laser 7 may excite the rubidium atom for spin polarization, and to be transferred to that of the potassium atom. In this case, the rubidium atom is excited by the pump light. Then, due to the spin exchange interaction between potassium and rubidium, the spin polarization of the rubidium atom transferss to the potassium atom, so that the potassium atom is excited.

The probe laser 8 emits probe light for detecting a change in the polarization angle caused by a magnetic field in the excited state of the alkali metal atom. The probe laser 8 may shape the probe light in any size. The probe laser 8 may emit probe light whose height is smaller than its width. When the probe light passes through the vapor of the alkali metal, the polarization angle changes due to the influence of the state of spin polarization of the alkali metal atom. By detecting this change in the polarization angle, the state of spin polarization can be derived. The wavelength of the probe light is set according to the type of atoms forming the alkali metal vapor (more specifically, the wavelength of the absorption line). For example, when only potassium is contained as an alkali metal in the cell 2, the wavelength of the probe light is detuned from the wavelength of the pump light (for example, 770.1 nm), and is set to, for example, about 770 nm. By detuning the wavelength of the probe light from the wavelength of the pump light, the absorption of the probe light by potassium is suppressed.

When potassium and rubidium are contained as alkali metals in the cell 2, the probe laser 8 may emit probe light for detecting a change in the polarization angle caused by a magnetic field in the excited state of the potassium atom. When two types of alkali metals are used as described above, it is preferable that the density of rubidium used for excitation is lower than that of potassium used for the probe. When the density of rubidium is low, the pump light reaches deep from the incidence end of the pump light, so that the rubidium can be uniformly excited even if the cell is elongated in the x-axis direction. Therefore, it is possible to obtain the uniform sensitivity.

The fiber connector 9 is a connector having a pump light inlet and a probe light inlet for introducing the pump light emitted from the pump laser 7 and the probe light emitted from the probe laser 8 into the housing of the optically pumped magnetometer 1. In addition, the fiber connector 9 may shape the pump light and the probe light in any size. The fiber connector 9 may adjust each of the pump light and the probe light to be in a parallel state by, for example, a collimating lens.

The pump laser 7 may emit the pump light in the same direction as an emission direction of the probe light from the probe laser 8. For example, the pump laser 7 and the probe laser 8 emit the pump light and the probe light in the negative direction of the x axis, respectively. The pump light emitted from the pump laser 7 and the probe light emitted from the probe laser 8 are guided to the fiber connector 9. In this case, the fiber connector 9 is arranged so that the pump light inlet is located in the positive direction of the z axis with respect to the probe light inlet. The emission directions of the pump light and the probe light of the fiber connector 9 are not limited to this.

The mirror 10 is a pump light mirror that reflects the pump light emitted from the pump laser 7. The mirror 10 is arranged in the negative direction of the x axis with respect to the pump light inlet of the fiber connector 9. The pump light is incident on the mirror 10 through the fiber connector 9. The mirror 10 reflects the pump light, which is emitted from the pump laser 7 in the negative direction of the x axis, in the negative direction (direction toward the scalp) of the z axis. The mirror 10 may be bonded to the peak frame 20 with an optical adhesive.

The mirror 11 is a pump light mirror that reflects the pump light, which is reflected by the mirror 10 in the negative direction (direction toward the scalp) of the z axis, in a first direction (positive direction of the x axis) along the scalp so that the pump light guided in the first direction (positive direction of the x axis) is incident on the cell 2. The mirror 11 is arranged in the negative direction of the z axis with respect to the mirror 10. The mirror 11 may be bonded to the pump light incidence surface 2*a* of the cell 2 with a heat-resistant optical adhesive.

The splitting unit 12 splits the probe light into multiple components. The splitting unit 12 is configured to include, for example, a beam splitter 12B S and a mirror 12M. The beam splitter 12B S reflects some of the incident light components and transmits the remaining light components. The mirror 12M reflects the incident light. The probe light is incident on the beam splitter 12B S through the fiber connector 9. The probe light transmitted through the beam splitter 12B S is incident on the mirror 12M.

The splitting unit 12 may be arranged on a side opposite to the scalp with the cell 2 interposed therebetween. The probe laser 8 may emit the probe light so that the probe light guided in a direction (negative direction of the x axis) opposite to the first direction is incident on the splitting unit 12. The splitting unit 12 may output each of the split probe light components in a direction (negative direction of the y axis) perpendicular to the first direction and along the scalp. For example, the beam splitter 12BS and the mirror 12M are arranged in the negative direction of the x axis with respect to the probe light inlet of the fiber connector 9. In this case, the fiber connector 9 guides the probe light in the negative direction of the x axis. The mirror 12M is located in the negative direction of the x axis with respect to the beam splitter 12BS. The beam splitter 12BS outputs some of the incident probe light components in the direction (negative direction of the y axis) perpendicular to the first direction and along the scalp, and transmits the remaining probe light components in the negative direction of the x axis. The mirror 12M reflects the incident probe light in the negative direction of the y axis. The beam splitter 12BS and the mirror 12M may be bonded to the peak frame 20 with an optical adhesive.

The number of split probe light components corresponds to the number of channels (ch) in which the optically pumped magnetometer 1 can measure the magnetic field. In addition, the number of components on the optical path of the probe light may also be different depending on the number of channels. For example, when the probe light is split into four probe light components (4 channels), the splitting unit 12 is configured to include beam splitters 12BSa, 12BSb, and 12BSc and the mirror 12M. The splitting unit 12 splits the probe light so that the four probe light components are approximately the same light component, that is, each of the four probe light components is a light component of 25% of the probe light before the splitting (before being guided by the splitting unit 12). For example, when the beam splitters 12BSa, 12BSb, and 12BSc are arranged in series in the negative direction of the x axis to transmit and split the probe light in this order, the transmittances of the beam splitters 12BSa, 12BSb, and 12BSc are different. For example, the transmittances of the beam splitters 12BSa, 12BSb, and 12BSc may be 75%, 66.6%, and 50%, respectively. In this case, the beam splitter 12BSa outputs 25% of the incident light components in the negative direction of the y axis and outputs the remaining 75% in the negative direction of the x axis. The beam splitter 12BSb outputs 33.3% of the light components transmitted through the beam splitter 12BSa in the negative direction of the y axis, and outputs the remaining 66.6% in the negative direction of the x axis. The beam splitter 12BSc outputs 50% of the light components transmitted through the beam splitter 12BSb in the negative direction of the y axis, and outputs the remaining 50% in the negative direction of the x axis. The mirror 12M reflects the light component transmitted through the beam splitter 12BSc in the negative direction of the y axis. By splitting the incident light in this manner, each of the four probe light components becomes a light component of 25% of the probe light before the splitting (before being guided by the splitting unit 12).

In FIG. 1B, the mirror 10 and the mirror 11 are omitted. As shown in FIG. 1B, the mirror 13 is a probe light mirror that reflects each probe light component obtained as a result of the splitting by the splitting unit 12. The mirror 13 reflects each probe light component obtained as a result of the splitting by the splitting unit 12 in the direction toward the scalp. The mirror 13 is arranged in the negative direction of the y axis with respect to the splitting unit 12. The mirror 13 reflects each probe light component, which is output in the negative direction of the y axis by the splitting unit 12, in the negative direction (direction toward the scalp) of the z axis.

The mirror 14 is a probe light mirror that causes each probe light component, which is guided in a second direction perpendicular to the first direction and along the scalp, to be incident on the cell 2. The second direction is, for example, the positive direction of the y axis. The mirror 14 further reflects each probe light component reflected by the mirror 13 in the second direction, so that each probe light component is incident on the cell 2. The mirror 14 is arranged in the negative direction of the z axis with respect to the mirror 13. Each probe light component reflected by the mirror 13 is incident on the mirror 14. The mirror 14 reflects each probe light component, which is guided in the negative direction of the z axis by the mirror 13, in the positive direction (second direction) of the y axis. Each probe light component reflected by the mirror 14 is incident perpendicular to the probe light incidence surface 2*b* of the cell 2. The mirror 14 may be bonded to the probe light incidence surface 2*b* of the cell 2 with a heat-resistant optical adhesive.

The mirror 15 reflects the incident probe light. The mirror 15 is arranged in the positive direction of the y axis with respect to the cell 2. Each probe light component that passes through the inside of the cell 2 and is emitted from the probe light emitting surface 2*c* of the cell 2 is incident on the mirror 15. The mirror 15 reflects each probe light component, which is incident through the probe light emitting surface 2*c* of the cell 2, in the positive direction (direction away from the scalp) of the z axis. The mirror 15 may be bonded to the probe light emitting surface 2*c* of the cell 2 with a heat-resistant optical adhesive.

The mirror 13, the mirror 14, and the mirror 15 may be configured as one mirror, or may be configured as multiple mirrors. For example, when the number of channels is four, the mirror 13 may be configured to include four mirrors 13*a*, 13*b*, 13*c*, and 13*d* (see FIG. 3B). Similarly, the mirror 14 may be configured to include four mirrors. Similarly, the mirror 15 may be configured to include four mirrors 15*a*, 15*b*, 15*c*, and 15*d*. Each mirror is arranged corresponding to the optical path of each of the four probe light components.

The polarized beam splitter 16 transmits a first light component, which is included in the incident light and has a first polarization angle, and outputs a second light component having another polarization angle from a surface different from the transmission surface, thereby splitting the incident light. For example, the first polarization angle is an angle inclined by 45° with respect to the polarization angle of the probe light emitted from the probe laser 8. The second light component is an angle inclined by 90° with respect to the first polarization angle. Therefore, when no magnetic field is applied to the cell 2, the amount of probe light having the first polarization angle and the amount of probe light having the second polarization angle are equal. In addition, when a magnetic field is applied, the spin polarization of the alkali metal atom changes, and the plane of polarization changes when the probe light passes through the inside of the cell 2. For this reason, the balance of the amount of light changes according to the magnetic field strength. The polarized beam splitter 16 is arranged in the positive direction of the z axis with respect to the mirror 15. Each probe light component reflected by the mirror 15 is incident on the polarized beam splitter 16. The polarized beam splitter 16 transmits the first light component included in each incident probe light component in the positive direction of the z axis. In addition, the polarized beam splitter 16 outputs the second light component included in each probe light component in the negative direction of the y axis.

The mirror 17 reflects the incident light. The mirror 17 is arranged in the negative direction of the y axis with respect to the polarized beam splitter 16. The second light component output from the polarized beam splitter 16 is incident on the mirror 17. The mirror 17 reflects the incident second light component in the positive direction of the z axis.

The first photodiode 18 and the second photodiode 19 are detection units that detect each probe light component, which is perpendicular to the pump light inside the cell 2. The first photodiode 18 is configured to include the same number of photodiodes as the number of channels (the number of probe light components obtained as a result of splitting by the splitting unit 12). The first photodiode 18 is arranged in the positive direction of the z axis with respect to the polarized beam splitter 16. The first light component transmitted through the polarized beam splitter 16 is incident on the first photodiode 18. The first photodiode 18 generates and outputs a signal corresponding to the intensity of the first light component. The second photodiode 19 is configured to include the same number of photodiodes as the number of channels. The second photodiode 19 is arranged in the positive direction of the z axis with respect to the mirror 17. The second light component reflected by the mirror 17 is incident on the second photodiode 19. The second photodiode 19 generates and outputs a second light signal corresponding to the intensity of the second light component.

The first photodiode 18 and the second photodiode 19 (detection units) are electrically connected to a derivation unit (not shown). For example, a control device 26 shown in FIG. 6 may have the function of the derivation unit. The derivation unit derives a change in the polarization angle corresponding to each probe light component based on the detection results of the first photodiode 18 and the second photodiode 19, and derives a magnetic field, which is relevant to the position (measurement location) of the brain corresponding to a region where each probe light component and the pump light are perpendicular to each other, from the change in the polarization angle corresponding to each probe light component.

In addition, for example, when the number of channels is four, the polarized beam splitter 16 may be configured to include four polarized beam splitters 16*a*, 16*b*, 16*c*, and 16*d*. Similarly, the mirror 17 may be configured to include four mirrors. In addition, the first photodiode 18 may be configured to include four first photodiodes 18*a*, 18*b*, 18*c*, and 18*d*. In addition, the second photodiode 19 may be configured to include four second photodiodes. In this case, each of the first photodiodes 18*a*, 18*b*, 18*c*, and 18*d* are paired with each of the four second photodiodes.

The peak frame 20 is a plate-shaped pedestal for bonding and fixing the case 6 in the negative direction of the z axis. A window for the optical paths of the pump light and the probe light may be provided in the peak frame 20.

The peak column 22 is a column for keeping the space between the peak frame 20 and the printed circuit board 21 constant.

The heat sink 23 is a heat dissipating component that is attached to the printed circuit board 21 in the positive direction of the z axis. The heat sink 23 dissipates heat from the inside (excluding the cell 2) of the housing of the optically pumped magnetometer 1 to adjust the internal temperature of the housing of the optically pumped magnetometer 1 so as to approach the external temperature (room temperature).

Figure 3A:
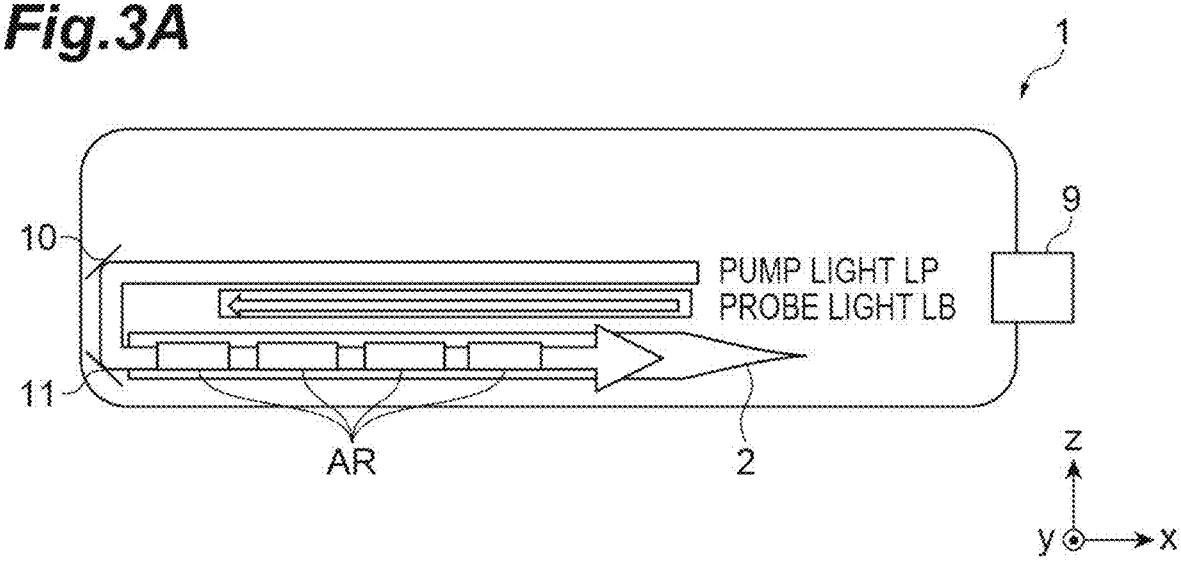
FIGS. 3A to 3C are schematic diagrams showing the optical paths of pump light and probe light.
Figure 3B:
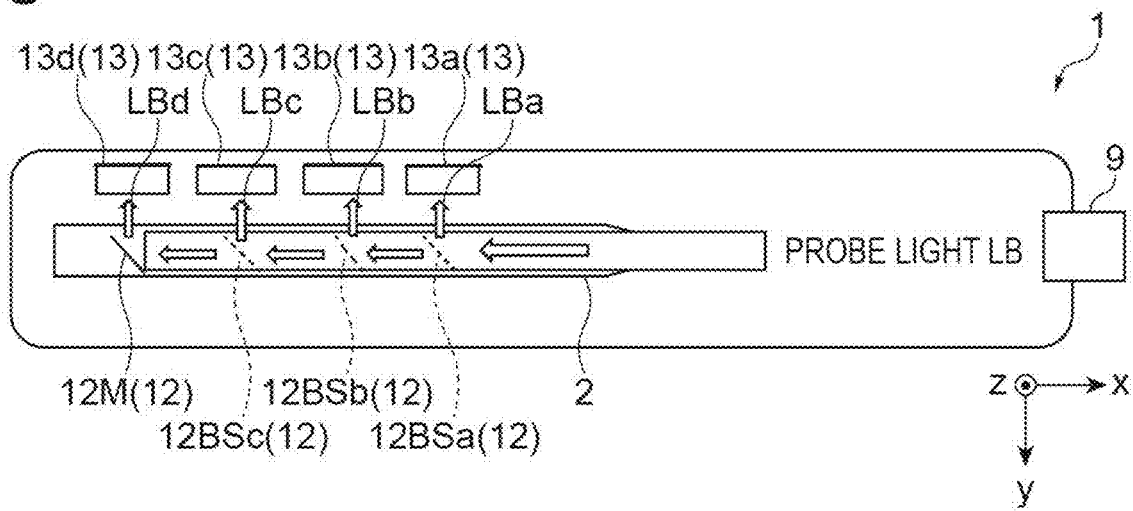
Figure 3C:
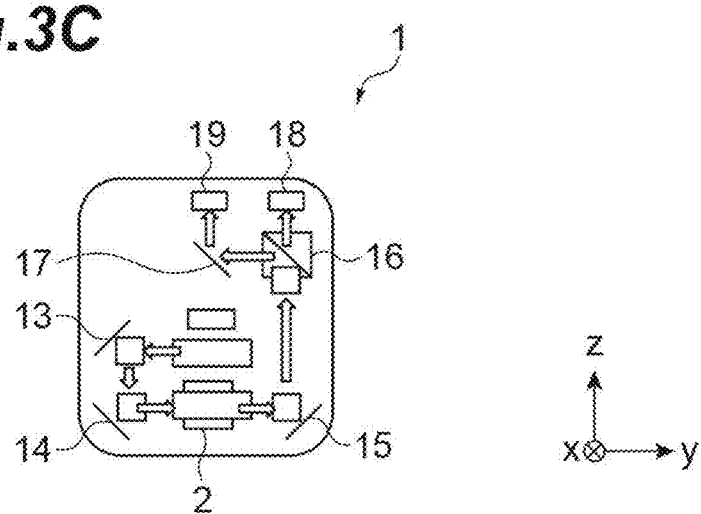

FIGS. 3A to 3C are schematic diagrams showing the optical paths of pump light and probe light. FIGS. 3A to 3C show the simplified configuration of the optically pumped magnetometer 1. In addition, FIGS. 3A to 3C show a case where the optically pumped magnetometer 1 has four channels. FIG. 3A is a side view of the optically pumped magnetometer 1, FIG. 3B is a top view of the optically pumped magnetometer 1, and FIG. 3C is a front view of the optically pumped magnetometer 1.

First, the optical path of the pump light will be described with reference to FIG. 3A. As shown in FIG. 3A, the pump laser 7 emits pump light LP in the negative direction of the x axis. The mirror 10 reflects the pump light LP incident through the fiber connector 9 in the negative direction of the z axis. Subsequently, the mirror 11 reflects the pump light LP reflected by the mirror 10 in the positive direction (first direction) of the x axis. In this manner, the pump light LP is incident on the cell 2 from the pump light incidence surface 2*a* and passes through the inside of the cell 2 in the first direction.

Next, the optical path of the probe light will be described. As shown in FIG. 3A, probe light LB emitted from the probe laser 8 is guided in the negative direction of the x axis through the fiber connector 9.

In FIG. 3B, the pump light LP is not shown. As shown in FIG. 3B, the splitting unit 12 is arranged in the positive direction (upper side) of the z axis with respect to the cell 2. The probe light LB emitted from the probe laser 8 in the negative direction of the x axis is incident on the splitting unit 12. The beam splitter 12BSa outputs a light component of 25% of the probe light LB as probe light LBa in the negative direction of the y axis, and transmits a light component of the remaining 75% in the negative direction of the x axis. The beam splitter 12BSb outputs a light component of 33.3% of the probe light transmitted through the beam splitter 12BSa, as probe light LBb, in the negative direction of the y axis, and transmits a light component of the remaining 66.6% in the negative direction of the x axis. Subsequently, the beam splitter 12BSc outputs a light component of 50% of the probe light transmitted through the beam splitter 12BSb, as probe light LBc, in the negative direction of the y axis, and transmits a light component of the remaining 50% in the negative direction of the x axis. Finally, the mirror 12M reflects the probe light transmitted through the beam splitter 12BSc as probe light LBd in the negative direction of the y axis. In this manner, the probe light LB is split into multiple probe light components LBa, LBb, LBc, and LBd. Each of the probe light components LBa, LBb, LBc, and LBd is a light component of 25% of the probe light LB before the splitting. Each of the probe light components LBa, LBb, LBc, and LBd is incident on the mirror 13 (mirrors 13a, 13b, 13c, and 13d) arranged in the negative direction of the y axis.

As shown in FIG. 3C, the mirror 13 (mirrors 13a, 13b, 13c, and 13d) reflects each probe light component output from the splitting unit 12 in the negative direction of the z axis. The mirror 14 (four mirrors) reflects each probe light component reflected by the mirror 13 in the positive direction (second direction) of the y axis. Each probe light component is incident from the probe light incidence surface 2b of the cell 2 and passes through the inside of the cell 2 in the second direction.

Once each probe light component passes through the inside of the cell 2, the probe light component is emitted from the probe light emitting surface 2c of the cell 2 to the outside of the cell 2. The mirror 15 (mirrors 15a, 15b, 15c, and 15d (see FIGS. 1A and 1B)) reflects each probe light component incident through the cell 2 in the positive direction of the z axis. Each probe light component is incident on the polarized beam splitter 16 arranged in the positive direction of the z axis when viewed from the mirror 15.

The polarized beam splitter 16 transmits a first light component, which is included in each incident probe light component, in the positive direction of the z axis, and outputs a second light component in the negative direction of the y axis. The first light component included in each probe light component is incident on the first photodiode 18 (first photodiodes 18a, 18b, 18c, and 18d (see FIG. 1A)). The second light component included in each probe light component is reflected by the mirror 17 (each of the four mirrors) in the positive direction of the z axis. Then, the second light component included in each probe light component is incident on the second photodiode 19 (each of the four second photodiodes).

As shown in FIG. 3A, regions AR indicate regions for four channels in which the pump light LP and the probe light are perpendicular to each other inside the cell 2. Specifically, the pump light LP travels through the cell 2 in the positive direction (first direction) of the x axis. Each probe light component travels in the positive direction (second direction) of the y axis inside the cell 2. The pump light LP in the first direction and the probe light in the second direction are perpendicular to each other inside the cell 2. A region for the measurement of magnetic field by the optically pumped magnetometer 1 is the region AR where the pump light and the probe light are perpendicular to each other inside the cell 2.

In addition, the pump light LP and each probe light component may be perpendicular to each other in the vicinity of a surface, on which a magnetic field is incident, inside the cell 2. Specifically, the positions of the cell 2, the mirror 11, and the mirror 14 may be adjusted so that the region where the pump light LP and each probe light component are perpendicular to each other is located near the magnetic field incidence surface 2e (see FIG. 2) of the cell 2.

Figure 4A:
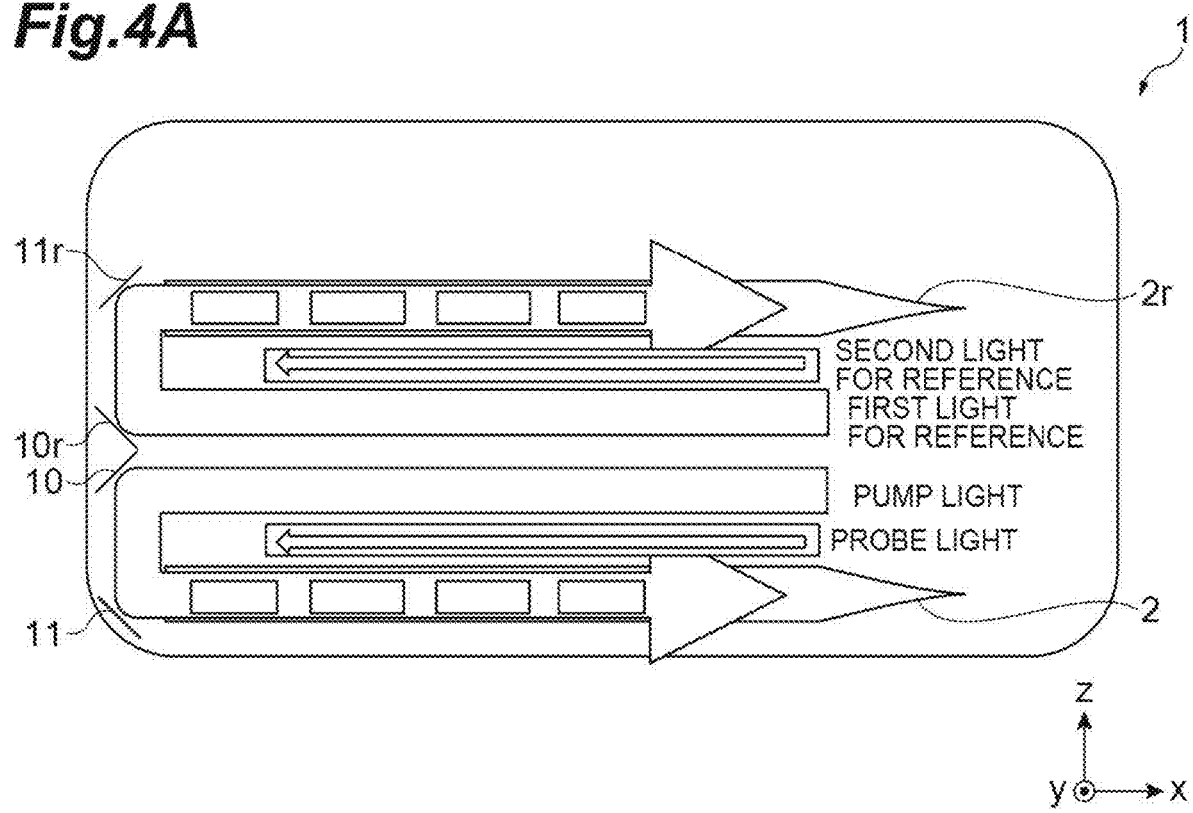
FIGS. 4A and 4B are schematic diagrams showing the optical paths of pump light and probe light in a 4-ch first-order differential axial gradiometer.
Figure 4B:
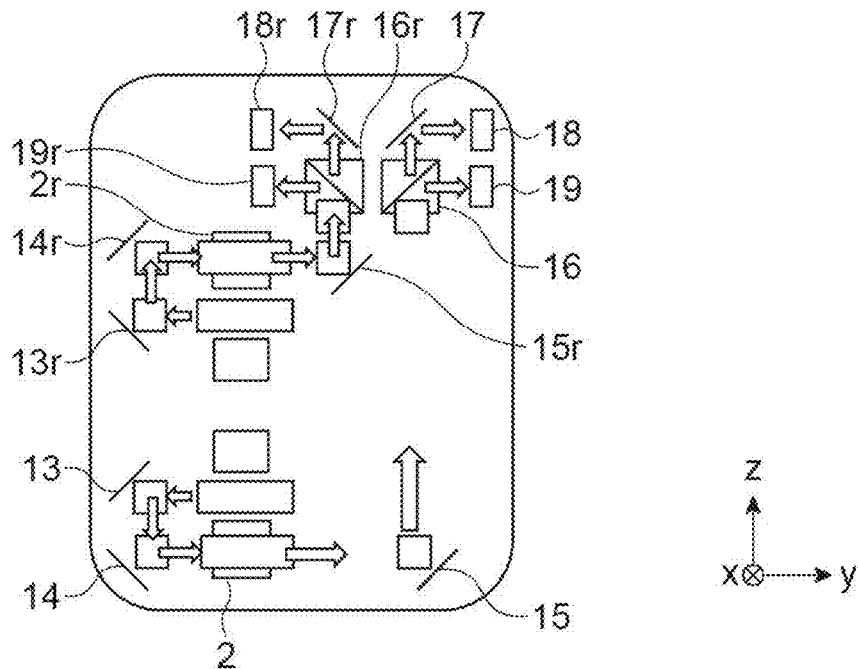

FIGS. 4A and 4B are schematic diagrams showing the optical paths of pump light and probe light in a 4-ch first-order differential axial gradiometer. In FIGS. 4A and 4B, the optically pumped magnetometer 1 further includes a reference cell 2r, a reference mirror 10r, a reference mirror 11r, a reference mirror 13r, a reference mirror 14r, a reference mirror 15r, a reference polarized beam splitter 16r, a reference mirror 17r, a first photodiode for reference 18r, and a second photodiode for reference 19r. These components correspond to the cell 2, the mirror 10, mirror 11, the mirror 13, the mirror 14, the mirror 15, the polarized beam splitter 16, the mirror 17, the first photodiode 18, and the second photodiode 19 in the measurement region (their functions match each other), respectively. The optically pumped magnetometer 1 may include components paired with other components (not shown).

The optically pumped magnetometer 1 may be configured as a first-order differential axial gradiometer further including the reference cell 2r (first member for reference), the first photodiode for reference 18r, and the second photodiode for reference 19r (second member for reference). The first member for reference is filled with alkali metal vapor and is arranged on a side opposite to the scalp with the cell 2 interposed therebetween, first light for reference guided in the first direction is incident in order to excite the alkali metal atom, and multiple second light components for reference guided in the second direction are incident in order to detect a change in the polarization angle caused by a magnetic field in the excited state of the alkali metal atom.

The second member for reference may detect multiple second light components for reference, which are perpendicular to the first light for reference inside the first member for reference, outside the first member for reference. Each region where each probe light component and the pump light are perpendicular to each other in the cell 2 may overlap a region where any of the second light components for reference and the first light for reference are perpendicular to each other in the first member for reference, in the direction perpendicular to the scalp. When deriving the change in the polarization angle corresponding to each probe light component detected by the first photodiode 18 and the second photodiode 19, the derivation unit (for example, the control device 26) may perform noise removal processing in consideration of the detection results of the first photodiode 18 and the second photodiode 19 with respect to each probe light component and the detection results of the first photodiode for reference 18r and the second photodiode for reference 19r with respect to the second light for reference whose region overlaps each probe light component in the direction perpendicular to the scalp. In addition, even if the reference cell 2r is not used, a planar gradiometer configuration may be used in which a location common to signals from adjacent channels of the cell 2 is removed as common mode noise.

Figure 5:
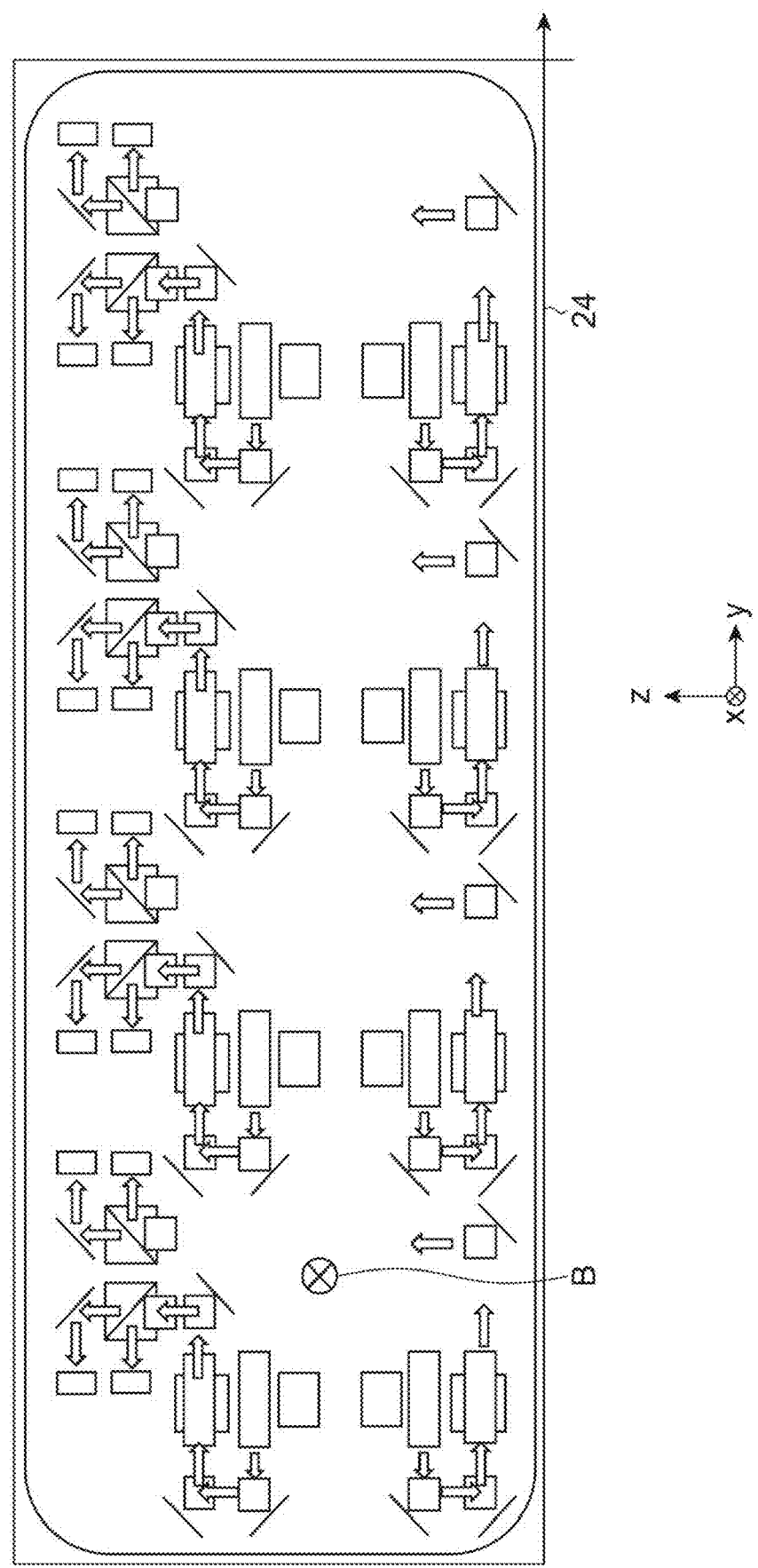
FIG. 5 is a schematic diagram showing a 4×4-ch first-order differential axial gradiometer.

FIG. 5 is a schematic diagram showing a 4×4-ch first-order differential axial gradiometer. The 4×4-ch first-order differential axial gradiometer is a modularization of four 4-ch first-order differential axial gradiometers using one housing, and measurement results for 16 channels can be obtained.

The optically pumped magnetometer 1 may include a bias magnetic field forming coil 24 that generates a bias magnetic field B in a region where the cell 2 is arranged according to a current supplied from a coil power supply (not shown). The bias magnetic field forming coil 24 can be, for example, a coil system surrounding the optically pumped magnetometer 1. The direction of the bias magnetic field B is, for example, the same direction (positive direction of the x axis) as the optical path of the pump light passing through the inside of the cell 2. By adjusting the strength of the bias magnetic field B, the peak frequency of the magnetic field sensitivity of the optically pumped magnetometer 1 can be adjusted. The peak frequency can be changed according to the object to be measured by the optically pumped magnetometer 1. For example, when the optically pumped magnetometer 1 is used for the measurement of the brain's magnetic field, it is desirable to match the peak frequency of the magnetic field sensitivity to several to several hundred Hz, which is the frequency band of the brain's magnetic field. Here, for example, when the coil wound around the first-order differential axial gradiometer forms the bias magnetic field B of 7 nT, the peak frequency of the optically pumped magnetometer 1 can be adjusted to 50 Hz.

Figure 6:
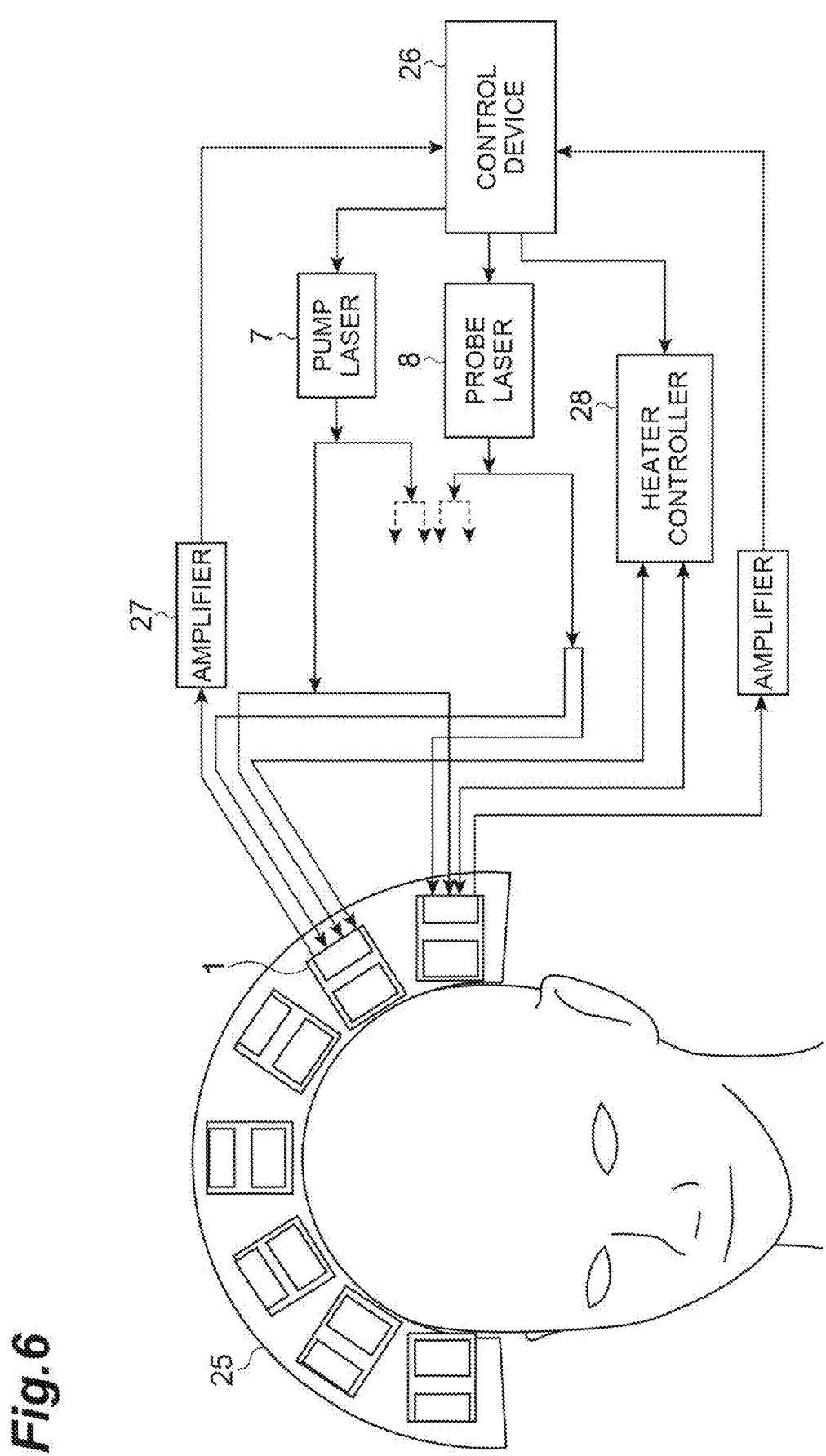
FIG. 6 is a schematic diagram showing a magnetoencephalograph using an optically pumped magnetometer.

FIG. 6 is a schematic diagram showing a magnetoencephalograph using the optically pumped magnetometer 1. The optically pumped magnetometer 1 may be, for example, a 4×4-ch first-order differential axial gradiometer. The magnetoencephalograph includes the optically pumped magnetometer 1, a non-magnetic frame 25, the control device 26, the pump laser 7, the probe laser 8, an amplifier 27, and a heater controller 28. The multiple optically pumped magnetometers 1 are arranged at predetermined intervals along the scalp, for example. For example, when twelve 4×4-ch first-order differential axial gradiometers are arranged at predetermined intervals along the scalp, the magnetoencephalograph can acquire measurement regions for 192 channels.

The non-magnetic frame 25 is a frame that covers the entire scalp of the subject whose brain's magnetic field is to be measured, and is formed of a non-magnetic material such as graphite. The non-magnetic frame 25 can be, for example, a helmet-type frame that surrounds the entire scalp of the subject and is attached to the head of the subject. Multiple optically pumped magnetometers 1 are fixed to the non-magnetic frame 25 so as to be close to the scalp of the subject.

The control device 26 is a device that obtains information regarding the magnetic field detected by the optically pumped magnetometer 1 by using the signal output from the amplifier 27. The control device 26 may be configured as a derivation unit. In addition, the control device 26 may control operations such as the emission timing and the emission time of the pump laser 7 and the probe laser 8.

The control device 26 is physically configured to include a memory such as a RAM and a ROM, a processor (arithmetic circuit) such as a CPU, a communication interface, and a storage unit such as a hard disk. Examples of the control device 26 include a personal computer, a cloud server, a smartphone, and a tablet terminal. The control device 26 functions by executing a program stored in the memory on the CPU of the computer system.

The pump light emitted from the pump laser 7 may be incident on each of the multiple optically pumped magnetometers 1 by fiber branching. In addition, the probe light emitted from the probe laser 8 may be incident on each of the multiple optically pumped magnetometers 1 by fiber branching.

The amplifier 27 is a device or circuit that amplifies an output result signal from the optically pumped magnetometer 1 and outputs the signal to the control device 26.

The heater controller 28 is a temperature adjusting device connected to the heater 3 for heating the cell of the optically pumped magnetometer 1 and the thermocouple 5 for measuring the temperature of the cell 2. The heater controller 28 adjusts the temperature of the cell 2 by receiving the temperature information of the cell 2 from the thermocouple 5 and adjusting the heating of the heater 3 based on the temperature information.

Figure 7:
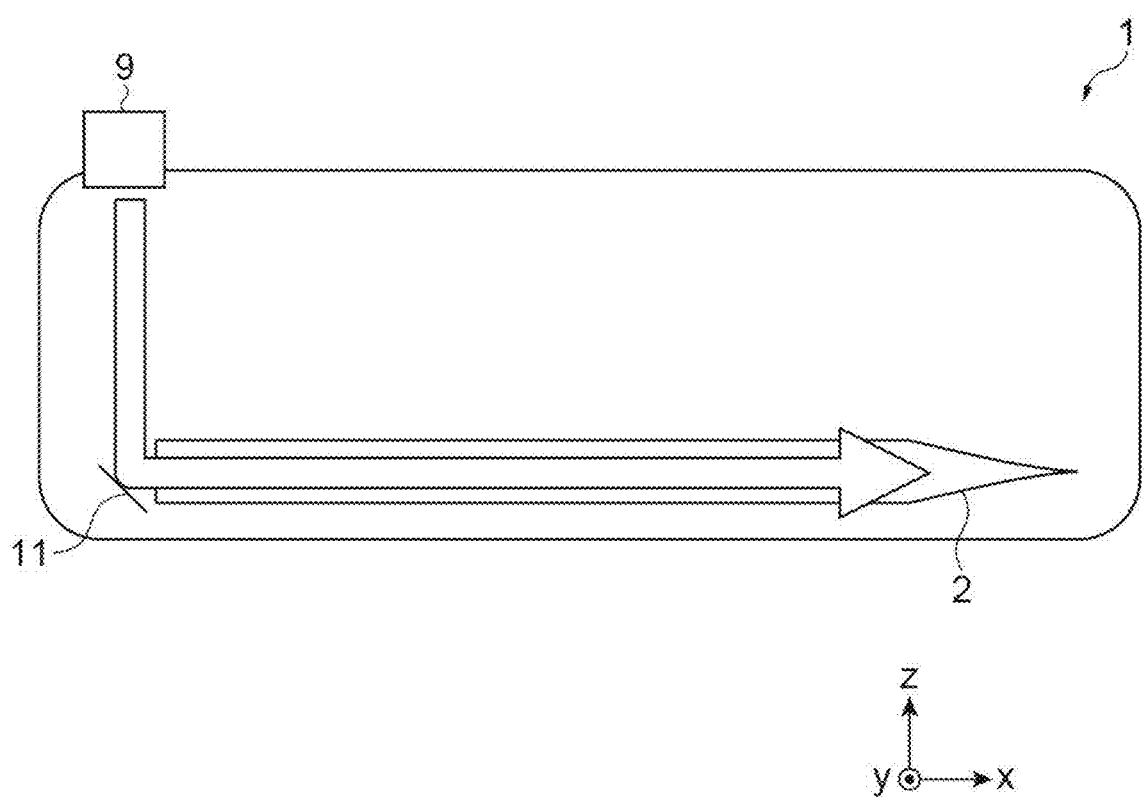
FIG. 7 is a schematic diagram showing another optical path of the pump light.

FIG. 7 is a schematic diagram showing another optical path of the pump light. The pump laser 7 may emit the pump light in a direction perpendicular to the emission direction (see FIG. 3A) of the probe light by the probe laser 8. For example, the pump laser 7 may emit the pump light in the negative direction of the z axis. The pump light emitted from the pump laser 7 is incident on the mirror 11 through the fiber connector 9. The mirror 11 reflects the incident pump light in the positive direction (first direction) of the x axis. The pump light is incident perpendicular to the pump light incidence surface 2a of the cell 2. In this manner, the pump light is guided to the pump light incidence surface 2a of the cell 2 only by the mirror 11. According to such a configuration, the mirror 10 is not necessary.

Figure 8:
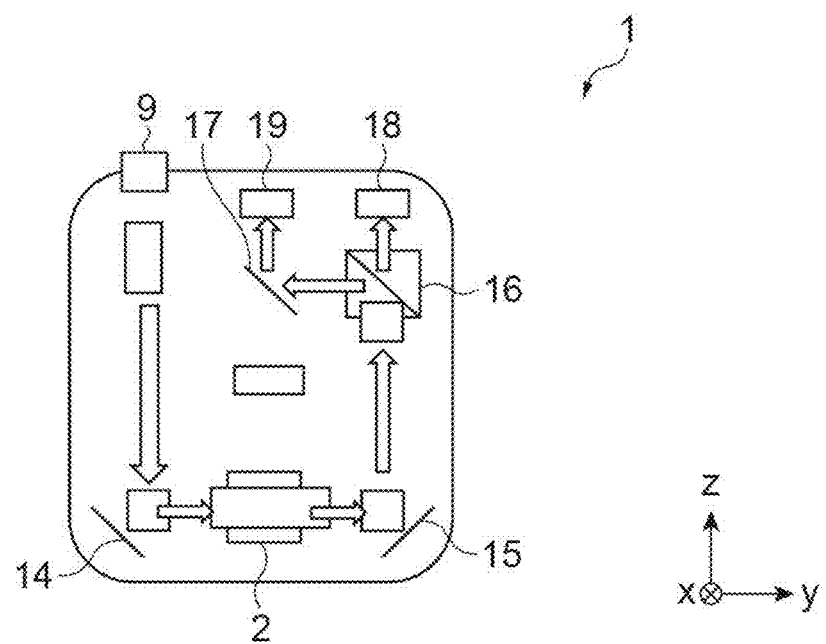
FIG. 8 is a schematic diagram showing another optical path of the probe light.

FIG. 8 is a diagram showing another optical path of the probe light. The probe laser 8 may emit the probe light in a direction toward the scalp. In FIG. 8, the probe light may be split in advance by fiber branching or the like. In this case, the fiber connector 9 may have as many probe light inlets as the number of channels. Each of the multiple probe light components emitted from the fiber connector 9 is incident on the mirror 14. The mirror 14 reflects each of the incident probe light components in the positive direction (first direction) of the y axis. Each of the multiple probe light components is incident perpendicular to the probe light incidence surface 2b of the cell 2. In this manner, the probe light is guided to the probe light incidence surface 2b of the cell 2 only by the mirror 14. According to such a configuration, multiple probe light inlets of the fiber connector 9 are necessary, but the splitting unit 12 and the mirror 13 are not necessary.

EXAMPLES

An example of the size when the optically pumped magnetometer 1 secures the measurement region for four channels is shown. The cell 2 may have a shape in which the length in the x-axis direction is 50 mm, the outer shape of the cross section perpendicular to the x-axis direction is 6×6 $mm^{2'}$, the inside of the cross section perpendicular to the x-axis direction is 4×4 $mm^{2'}$, and the glass thickness is 1 mm. The pump laser 7 or the fiber connector 9 may shape the pump light such that the height of the pump light is 3.5 mm and the width is 3.5 mm, for example. In addition, the probe laser 8 or the fiber connector 9 may shape the probe light such that the height of the probe light is 2 mm and the width is 8 mm, for example. Then, in the x-axis direction, the interval between adjacent channels may be 2 mm Since the width of the probe light is 8 mm and the interval between the adjacent channels is 2 mm, the width for the four channels can be secured if the length of the cell 2 in the x-axis direction is about 50 mm With such a 4-channel optically pumped magnetometer 1, it is possible to obtain four measurement regions of 3.5×2×8 $mm^3$ Thus, when multiple optically pumped magnetometers 1 having multiple channels are arranged in the first direction in one housing, the interval between the measurement locations of the adjacent optically pumped magnetometers 1 can be reduced. The pump light and the probe light described above can be shaped in any size.

In addition, for example, the width of each of the mirror 13, the mirror 14, and the mirror 15 for reflecting the probe light in the height direction may be a width (for example, 2 mm) approximately the same as the height of the probe light. By using the mirror 13, the mirror 14, and the mirror 15 having such a width, it is possible to reduce the size of the optically pumped magnetometer 1 in the second direction. For example, the total width of the mirror 14 (width: 2 mm), the cell 2 (outer shape of the cross section perpendicular to the x-axis direction: 6×6 $mm^2$), and the mirror 15 (width: 2 mm) is 10 mm.

[Operational Effects]

Next, the operational effects of the optically pumped magnetometer 1 according to the above embodiment will be described.

The optically pumped magnetometer 1 according to the present embodiment includes: the cell 2 that is arranged along the measurement target and is filled with vapor of the alkali metal; the pump laser 7 that emits pump light for exciting the atom of the alkali metal; one or more pump light mirrors that reflect the pump light emitted from the pump laser 7 and cause the pump light guided in the first direction along the measurement target to be incident on the cell 2; the probe laser 8 that emits probe light for detecting a change in the polarization angle caused by a magnetic field in the excited state of the alkali metal atom; the splitting unit 12 that splits the probe light into multiple light components; one or more probe light mirrors that reflect probe light components, which are obtained as a result of the splitting by the splitting unit 12, and cause each of the probe light components guided in the second direction along the measurement target, which is a direction perpendicular to the first direction, to be incident on the cell 2; a detection unit that detects each of the probe light components perpendicular to the pump light inside the cell 2; and a derivation unit that derives a change in the polarization angle corresponding to each of the probe light components based on a detection result of the detection unit and derives a magnetic field, which is relevant to a measurement location corresponding to a region where each of the probe light components and the pump light are perpendicular to each other, from the change in the polarization angle corresponding to each of the probe light components.

In the optically pumped magnetometer 1 according to the present embodiment, the pump light guided in the first direction along the measurement target is incident on the cell 2 filled with alkali metal vapor, and each of the multiple probe light components obtained as a result of the splitting by the splitting unit 12 and guided in the second direction along the measurement target, which is a direction perpendicular to the first direction, is incident on the cell filled with alkali metal vapor. Then, by deriving the change in the polarization angle caused by the spin polarization corresponding to each probe light component passing through the cell 2, the magnetic field corresponding to the region where the pump light and each probe light component are perpendicular to each other inside the cell 2 is derived. As described above, in the optically pumped magnetometer 1 according to the present embodiment, since the probe light is split into multiple light components, it is not necessary to prepare the probe laser 8 for each region where the pump light and each probe light component are perpendicular to each other. Therefore, the configuration of the probe laser 8 is simplified. In addition, in such an optically pumped magnetometer 1, the probe light is split into multiple light components, and multiple channels are measured inside a single cell. Therefore, compared with a case where the probe light is not split, the interval between the measurement locations can be reduced. As described above, according to the present embodiment, it is possible to provide the optically pumped magnetometer 1 capable of reducing the interval between the measurement locations.

The probe laser 8 may emit probe light whose height is smaller than its width. By emitting the probe light having a large width in this manner, the region where the pump light and the probe light are perpendicular to each other becomes large. Therefore, it is possible to improve the measurement accuracy of the optically pumped magnetometer 1.

The alkali metal may be potassium and rubidium, the pump laser 7 may excite the atom of the rubidium for spin polarization, and to be transferred to that of the potassium, and the probe laser 8 may emit probe light for detecting a change in the polarization angle caused by a magnetic field in the excited state of the potassium atom. According to such a configuration, when the pump light excites the rubidium atom, the spin polarization of the rubidium atom transfers to the potassium atom to excite the potassium atom. By using such a spin exchange interaction between potassium and rubidium, the potassium atom can be uniformly excited as compared with a case where only the potassium atom is excited. This effect becomes noticeable by making the density of rubidium lower than the density of potassium. In addition, by using potassium having a high magnetic field sensitivity among alkali metals, it is possible to improve the measurement accuracy of the optically pumped magnetometer 1.

The pump light and each of the probe light components may be perpendicular to each other in the vicinity of a surface, on which a magnetic field is incident, inside the cell 2. According to such a configuration, since the pump light and each probe light component are perpendicular to each other at a position where the magnetic field is more strongly received, it is possible to improve the measurement accuracy of the optically pumped magnetometer 1.

At least one of the pump light mirrors and at least one of the probe light mirrors may be bonded to the cell 2 with an adhesive. According to such a configuration, since the pump light mirror and the probe light mirror are fixed to the cell 2, no space is generated between the cell 2 and each of the mirrors. As a result, the mirrors can be arranged stably and compactly.

The splitting unit 12 may be arranged on a side opposite to the measurement target with the cell 2 interposed therebetween. The probe laser 8 may emit the probe light so that the probe light guided in a direction opposite to the first direction is incident on the splitting unit 12. The splitting unit 12 may output each of the split probe light components in a direction perpendicular to the first direction and along the measurement target. One of the two probe light mirrors may reflect each of the probe light components, which are obtained as a result of the splitting by the splitting unit 12, in a direction toward the measurement target, and the other one of the two probe light mirrors may further reflect each of the probe light components reflected by the one probe light mirror in the second direction and cause each of the probe light components to be incident on the cell 2. According to such a configuration, it is possible to set the optical path of the probe light along the surface of the cell 2. Since the optical path of the probe light is set along the surface of the cell 2, the space is saved. Therefore, it is possible to reduce the size of the optically pumped magnetometer 1.

The optically pumped magnetometer 1 according to the present embodiment may further include: a first member for reference which is filled with the alkali metal vapor and is arranged on a side opposite to the measurement target with the cell 2 interposed therebetween, on which first light for reference guided in the first direction is incident in order to excite the alkali metal atom, and on which multiple second light components for reference guided in the second direction are incident in order to detect a change in the polarization angle caused by a magnetic field in the excited state of the alkali metal atom; and a second member for reference that detects the multiple second light components for reference perpendicular to the first light for reference inside the first member for reference, outside the first member for reference. Each region where each of the probe light components and the pump light are perpendicular to each other in the cell 2 overlaps a region where any of the second light components for reference and the first light for reference are perpendicular to each other in the first member for reference, in a direction perpendicular to the measurement target. When deriving a change in the polarization angle corresponding to each of the probe light components detected by the detection unit, the derivation unit performs noise removal processing in consideration of a detection result of the detection unit with respect to each of the probe light components and a detection result of the second member for reference with respect to the second light for reference whose region overlaps each of the probe light components in the direction perpendicular to the measurement target. The optically pumped magnetometer is configured as a first-order differential axial gradiometer. According to such a configuration, since the influence of the common mode noise is shown in the detection result of the detection unit with respect to each probe light component and the detection result of the second member for reference with respect to the second light for reference, the common mode noise can be removed by acquiring the difference between the output results of both. As a result, it is possible to improve the measurement accuracy of the optically pumped magnetometer 1.

The pump laser 7 may emit the pump light in the same direction as an emission direction of the probe light from the probe laser 8. According to such a configuration, since a pump light inlet and a probe light inlet are arranged at one place or places close to each other, the configuration of the optically pumped magnetometer 1 can be simplified.

The pump laser 7 may emit the pump light in a direction perpendicular to an emission direction of the probe light from the probe laser 8. In the region where the pump light and the probe light are perpendicular to each other inside the cell 2, the emission directions of the pump laser 7 and the probe laser 8 are perpendicular to each other. Therefore, it is possible to simplify the configuration of the mirrors including the pump light mirror and the probe light mirror.

What is claimed is:

1. An optically pumped magnetometer comprising:
   a cell arranged along a measurement target and filled with vapor of an alkali metal;
   a pump laser configured to emit pump light for exciting an atom of the alkali metal;
   one or more pump light mirrors configured to reflect the pump light emitted from the pump laser and cause the pump light guided in a first direction along the measurement target to be incident on the cell;
   a probe laser configured to emit probe light for detecting a change in a polarization angle caused by a magnetic field in an excited state of the alkali metal atom;
   a splitting unit comprising beam splitters configured to split the probe light into multiple light components;
   probe light mirrors configured to reflect the probe light components obtained as a result of the splitting by the splitting unit, and cause each of the probe light components guided in a second direction along the measurement target and perpendicular to the first direction, to be incident on the cell;
   a detection unit configured to detect each of the probe light components perpendicular to the pump light inside the cell; and
   a derivation unit configured to derive a change in the polarization angle corresponding to each of the probe light components based on a detection result of the detection unit and derive a magnetic field relevant to a measurement location of the measurement target corresponding to a region where each of the probe light components and the pump light are perpendicular to each other, from the change in the polarization angle corresponding to each of the probe light components,
   wherein the splitting unit is arranged on a side opposite to the measurement target with the cell interposed therebetween,
   the probe laser is arranged to emit the probe light so that the probe light is guided in a direction opposite to the first direction and is incident on the splitting unit,
   the splitting unit outputs each of the split probe light components in a direction perpendicular to the first direction and along the measurement target, and
   one of the two probe light mirrors reflects each of the probe light components obtained as a result of the splitting by the splitting unit, in a direction toward the measurement target, and the other one of the two probe light mirrors further reflects each of the probe light components reflected by the one probe light mirror in the second direction and causes each of the probe light components to be incident on the cell.

2. The optically pumped magnetometer according to claim 1,
   wherein the probe laser emits probe light whose height is smaller than its width in cross-section.

3. The optically pumped magnetometer according to claim 1,
   wherein the alkali metal is potassium and rubidium,
   the pump laser excites an atom of the rubidium for spin polarization to be transferred to that of the potassium, and
   the probe laser emits probe light for detecting a change in a polarization angle caused by a magnetic field in an excited state of the potassium atom.

4. The optically pumped magnetometer according to claim 1,
   wherein the pump light and each of the probe light components are perpendicular to each other near a magnetic field incidence surface of the cell on which a magnetic field generated from the measurement target is incident.

5. The optically pumped magnetometer according to claim 1,
   wherein at least one of the pump light mirrors and at least one of the probe light mirrors are bonded to the cell with an adhesive.

6. The optically pumped magnetometer according to claim 1,
   wherein the pump laser emits the pump light in the same direction as an emission direction of the probe light from the probe laser.

7. The optically pumped magnetometer according to claim 1,
   wherein the pump laser emits the pump light in a direction perpendicular to an emission direction of the probe light from the probe laser.

8. An optically pumped magnetometer, comprising:
   a cell arranged along a measurement target and filled with vapor of an alkali metal;
   a pump laser configured to emit pump light for exciting an atom of the alkali metal;
   one or more pump light mirrors configured to reflect the pump light emitted from the pump laser and cause the pump light guided in a first direction along the measurement target to be incident on the cell;

a probe laser configured to emit probe light for detecting a change in a polarization angle caused by a magnetic field in an excited state of the alkali metal atom;

a splitting unit comprising beam splitters configured to split the probe light into multiple light components;

probe light mirrors configured to reflect the probe light components obtained as a result of the splitting by the splitting unit, and cause each of the probe light components guided in a second direction along the measurement target and perpendicular to the first direction, to be incident on the cell;

a detection unit configured to detect each of the probe light components perpendicular to the pump light inside the cell;

a derivation unit configured to derive a change in the polarization angle corresponding to each of the probe light components based on a detection result of the detection unit and derive a magnetic field relevant to a measurement location of the measurement target corresponding to a region where each of the probe light components and the pump light are perpendicular to each other, from the change in the polarization angle corresponding to each of the probe light components;

a first member for reference being filled with the alkali metal vapor and arranged on a side opposite to the measurement target with the cell interposed therebetween, the first member for reference being configured such that a first light for reference guided in the first direction is incident thereon in order to excite the alkali metal atom of the first member for reference, and multiple second light components for reference guided in the second direction are incident thereon in order to detect a change in the polarization angle caused by a magnetic field in the excited state of the alkali metal atom of the first member for reference; and a second member for reference configured to detect the multiple second light components for reference perpendicular to the first light for reference inside the first member for reference, outside the first member for reference, wherein each region where each of the probe light components and the pump light are perpendicular to each other in the cell overlaps a respective region where any of the second light components for reference and the first light for reference are perpendicular to each other in the first member for reference, in a direction perpendicular to the measurement target, when deriving a change in the polarization angle corresponding to each of the probe light components detected by the detection unit, the derivation unit performs noise removal processing in consideration of a detection result of the detection unit with respect to each of the probe light components and a detection result of the second member for reference with respect to the multiple second light components for reference whose region overlaps each of the probe light components in the direction perpendicular to the measurement target, and the optically pumped magnetometer is configured as a first-order differential axial gradiometer.

9. The optically pumped magnetometer according to claim 8, wherein the probe laser emits probe light whose height is smaller than its width in cross-section.

10. The optically pumped magnetometer according to claim 8, wherein the alkali metal is potassium and rubidium, the pump laser excites an atom of the rubidium for spin polarization to be transferred to that of the potassium, and the probe laser emits probe light for detecting a change in a polarization angle caused by a magnetic field in an excited state of the potassium atom.

11. The optically pumped magnetometer according to claim 8, wherein the pump light and each of the probe light components are perpendicular to each other near a magnetic field incidence surface of the cell on which a magnetic field generated from the measurement target is incident.

12. The optically pumped magnetometer according to claim 8, wherein at least one of the pump light mirrors and at least one of the probe light mirrors are bonded to the cell with an adhesive.

13. The optically pumped magnetometer according to claim 8, wherein the pump laser emits the pump light in the same direction as an emission direction of the probe light from the probe laser.

14. The optically pumped magnetometer according to claim 8, wherein the pump laser emits the pump light in a direction perpendicular to an emission direction of the probe light from the probe laser.

* * * * *